US012551362B2

(12) United States Patent
Gorski

(10) Patent No.: US 12,551,362 B2
(45) Date of Patent: Feb. 17, 2026

(54) TENNIS ELBOW OFFLOADING DEVICE

(71) Applicant: Jerrold Marlon Gorski, Old Westbury, NY (US)

(72) Inventor: Jerrold Marlon Gorski, Old Westbury, NY (US)

( * ) Notice: Subject to any disclaimer, the term of this patent is extended or adjusted under 35 U.S.C. 154(b) by 0 days.

(21) Appl. No.: 19/185,926

(22) Filed: Apr. 22, 2025

(65) Prior Publication Data

US 2025/0262081 A1 Aug. 21, 2025

(51) Int. Cl.
*A61F 5/01* (2006.01)
*A61F 5/30* (2006.01)

(52) U.S. Cl.
CPC .............. *A61F 5/0118* (2013.01); *A61F 5/30* (2013.01)

(58) Field of Classification Search
CPC ...... A61F 5/0118; A61F 5/013; A61F 13/107; A61F 5/0109
USPC .......................................................... 602/20
See application file for complete search history.

(56) References Cited

U.S. PATENT DOCUMENTS 5,063,913 A * 11/1991 Nyi ........................ A61F 13/107 602/20
5,624,388 A * 4/1997 Lehr ...................... A61F 5/0118 602/20
2005/0215933 A1* 9/2005 Stearns ................. A61F 5/0118 602/57
2009/0131842 A1* 5/2009 Rodgers, Jr. ........ G06Q 30/0601 705/26.1
2014/0031733 A1* 1/2014 Martino ................ A61F 5/0118 602/20

* cited by examiner

*Primary Examiner* — Rachael E Bredefeld
*Assistant Examiner* — Seth R. Brown

(57) ABSTRACT

A wearable pressure-relief brace has been developed to treat tennis elbow by redistributing forces away from the lateral epicondyle. Unlike prior art, which primarily relies on compression to alleviate symptoms, this innovation addresses the root cause of prolonged pain and delayed healing: repetitive nighttime pressure on injured elbow tissues during side sleeping. Referenced research highlights how such pressures exacerbate the initial sprain or strain of the common extensors at their origin at the lateral epicondyle. The described apparatus minimizes these aggravating forces, enabling rapid relief and recovery. This offloading brace represents a significant advancement over passive restraints, offering improved protection, comfort, freedom of movement, and compliance, particularly during sleep.

2 Claims, 4 Drawing Sheets

TENNIS ELBOW OFFLOADING DEVICE

CROSS-REFERENCE TO RELATED REFERENCE

The current nonprovisional application claims a benefit to the U.S. Provisional Patent application No. 63/731,552 dated May 17, 2024.

FEDERALLY SPONSORED RESEARCH

Not Applicable

REFERENCE TO SEQUENCE LISTING

Not Applicable

BACKGROUND OF THE INVENTION

In the field of Medicine, tennis elbow (also known as lateral epicondylitis and lateral epicondylosis) is a painful self-limited chronic elbow condition that is poorly understood. The cause of tennis elbow beyond the initial injury is unknown. Tennis Elbow is characterized by delayed healing and prolonged pain after an initial sprain/strain injury. Many different types of therapeutic devices exist and different surgical procedures have been devised in attempts to mitigate the pain of the condition. None of the former treatments are based upon an understanding of the root cause and are of little if any benefit. Many devices of prior art are variations of patent # U.S. Pat. No. 3,789,842A a strap like device applied below the elbow. These devices generally utilize compression of the muscles and tissues in the forearm based on speculation that additional pressure will minimize the tensile or other forces pulling on injured tissues and thus reduce pain. Without an understanding of the root cause, the devices of prior art are generally ineffective in providing pain relief, or reducing the time to healing. An explanation was necessary to explain why an acute sprain would transition into a chronic painful condition requiring up to two years to improve. A reasonable expectation is that a sprain elsewhere for example, an ankle sprain, typically heals in 8-12 weeks.

This inventor had first considered the novel concept of a "pathological sleep position" in another medical condition, specifically neck pain. On that basis, he hypothesized that the severe morning complaints typically reported in tennis elbow might likewise be due to a pathological sleep position. More specifically, a nocturnal application of pressures on the lateral epicondyle of the elbow would repetitively aggravate an acute primary sprain/strain and delay healing. A prospective therapeutic trial was conducted in tennis elbow by changing the sleep position. The results were encouraging but there were some concerns later addressed by this invention.

The original tennis elbow injury is believed to result from microscopic tears, known more commonly as sprain/strains. These are the result of trauma, overuse or a combination of these mechanical factors, and not solely from playing tennis (resulting from hitting a back handed off center torqueing or racket twisting mechanism). The location of the sprains, and most of the pain, are typically on the outer aspect of the elbow, where the origin of the hand and wrist extensors attach at the lateral epicondyle at the distal Humerus bone. Only approximately 5% of tennis elbow is due to playing tennis and the rest of this common condition (between 1 and 3 million in the United States) is more commonly diagnosed in craftsperson's and laborers. The naming of this condition has undergone multiple changes since the cause is obscure. Recent treatment recommendations include letting the condition run its natural course with waiting, reassurance, ice and analgesics. Avoiding surgery, injections, and unproven therapies are also currently advised.

A pathological sleep position was hypothesized, identified, analyzed and the results were published in a peer reviewed Global Journal of the American Academy of Orthopedic Surgeons (DOI: 10.5435/JAAOSGlobal-D-19-00082). The delay in healing of the acute primary sprain/strain injury of tennis elbow was due to repetitive nightly aggravation of a primary sprain in a habitual and very common position of sleep. The current novel invention was developed to address the restrictions and poor compliance inherent in using a passive restraint. The current invention has not been publicly disclosed except in a provisional patent application. The methodology to investigate pathological sleep positions, is a diagnostic and a therapeutic claim that is made in this invention.

A search of the prior art failed to reveal any similar ideological basis or practical application of the findings, nor the functional results of the invention disclosed herein.

This inventor has now aggregated other conditions associated with pathological sleep positions. This includes chronic idiopathic neck pain, carpal tunnel syndrome, cubital tunnel syndrome, plantar fasciitis, and GERD (reflux disease). In these conditions symptoms are present in the morning or at night. This invention validates the existence of some sleep positions causing aggravation. Those skilled in the art will understand that whereas this invention is disclosed in the present embodiment, that the method has widespread potential applications and alternative embodiments for other anatomical areas.

BRIEF SUMMARY OF THE INVENTION

Pressure is normally applied to a lateral epicondyle of the elbow by the weight of the arm on the sheets, bed and mattress when sleeping on the side in one of the most common sleep positions. Since sleep positions are extremely habitual, even after an injury we may assume these same positions. In tennis elbow, users characteristically awaken in the morning with severe morning complaints, which may be the only clue to a care provider to consider a pathological sleep position. A tennis elbow injury involves the sprained soft tissues on the lateral epicondyle. These injured soft tissues may undergo pressures while asleep that can aggravate and cause delays in healing and chronic pain. The most common sleeping position is on the side, as shown in FIG. 2. This demonstrates how pressure from the weight of an arm is applied to the lateral epicondyle. Since sleep positions are extremely habitual, and because sleep is defined as an unconscious state of mind a user is unable to consciously take corrective measures to a sleep position. The elbow brace described in this invention consists of an offloading ring integrated into a circumferential tubular sleeve that reduces pressures over the lateral epicondyle of a user. The instructions for this invention are to apply it to the elbow before going to sleep, and to wear it while asleep at night with the offloading ring surrounding the lateral epicondyle which is identified by pain and prominence of the bone. The geometry of the offset of the ring design described herein, limits the application of pressure on the lateral epicondyle by limiting or eliminating contact between the bed and the lateral epicondyle. The offset ring shifts the forces of this point contact from the lateral epicondyle and onto surrounding tissues. This prevents a repetitive nightly trauma and aggravation and allows for natural healing to occur. It was shown in a prior clinical study, that by successfully changing the sleep position of the upper extremity with the use of a passive restraint, that rapid relief and clinical healing were the result, usually within one month. However, compliance with the restraint was variable so a search was made to improve compliance resulting in the current invention. The benefit of this device is that it moves freely and independently with the elbow without the need for a passive restraint and it also offloads and removes pressure on the lateral epicondyle at the same time. It is comfortable, adjustable, easy to apply, understand, use, effective, and affordable. This device's main goal reduces and eliminates pressure on the lateral epicondyle, and it prevents nightly aggravation of a a sprain/strain, enabling natural healing to occur.

The sleeve maintains the position throughout the night. Although this application is suggested for use mainly at nighttime, this is not an exclusive application if a situation or circumstance exists wherein daytime protection from local pressure and aggravation on the lateral epicondyle is needed. The ring is placed surrounding the lateral epicondyle and held in place in this embodiment by a stretchy elastomeric knit circular sleeve, rubberized tubular sock, or a neoprene, spandex or elastic tubular sleeve or another material. It should not be limited by the preferred description in this embodiment as circular straps, rubber bands and compression wrappings can be applied to hold the sleeve and ring in place if needed. Hook and loop straps, glue or another adhesive may prove beneficial to hold the ring in place. Heat sensitive adhesives or injection molding might be utilized. This embodiment allows for full range of motion of the elbow without restraint. While this invention is indicated for tennis elbow, the concept of the unloading ring might also be considered for other conditions, but not limited to, for example Golfers Elbow, Pes Bursitis, Olecranon Bursitis, and Trochanteric Bursitis to reduce external pressure on a body part. The instructions for use are to apply the offloader device prior to sleep, and to wear all night, or as needed during day time. The lateral epicondyle is the prominence easily palpable on the outside of the elbow. The device is made from EVA foam, which is only one example. The material of the ring should be soft but not too compressible or deformable. The ring can be 3D printed. Other materials are considered as similar and might include rings made from plastics, Styrofoam, gel, air or water or gel filled ring shaped balloons or bladders and are included in the spirit of the art in this invention. The success of this invention proves that pathological sleep positions can cause injury due to pressure and aggravation and suggests that other unexplained and even chronic conditions characterized by complaints of insomnia, nocturnal pains or morning complaints may be the result of a pathological sleep position. Musculoskeletal aspects of sleep have not been widely studied even though nocturnal complaints are common.

BRIEF DESCRIPTION OF THE SEVERAL VIEWS OF THE DRAWING

FIG. 1A is a frontal elevation view and FIG. 1B is a side elevation view. The frontal elevation FIG. 1A shows the outer ring 102 which in this embodiment consists of a solid material (EVA foam). The inner aspect of the foam ring 102 in FIG. 1A has a rounded over edge 106. The outer edges 104 and 105 of the foam ring 102 in FIG. 1B are also rounded over. A space exists between 104 and 105 seen in the side elevation of FIG. 1B, to increase flexibility and contouring of the ring to a user's arm, while still allowing force transfers. The empty opening in the ring 103 in FIG. 1A, protects the lateral epicondyle from any contact and potential pressure on the soft tissues attached to the lateral epicondyle. The shape and dimensions of this opening might be changed if necessary from the depicted round to another shape. Practitioners of the art may envision modification of the essential spirit of this design such as application of sweat absorbing materials and other variations such as different materials.

FIG. 4 shows the ring 101 applied to the lateral side of the elbow with the empty center of the ring 103 surrounding the lateral epicondyle 407. The upper arm is depicted by number 402. The lower arm is number 403. The sleeve 201 is shown extending above and below the elbow joint.

DETAILED DESCRIPTION OF THE INVENTION

Figure 1A:
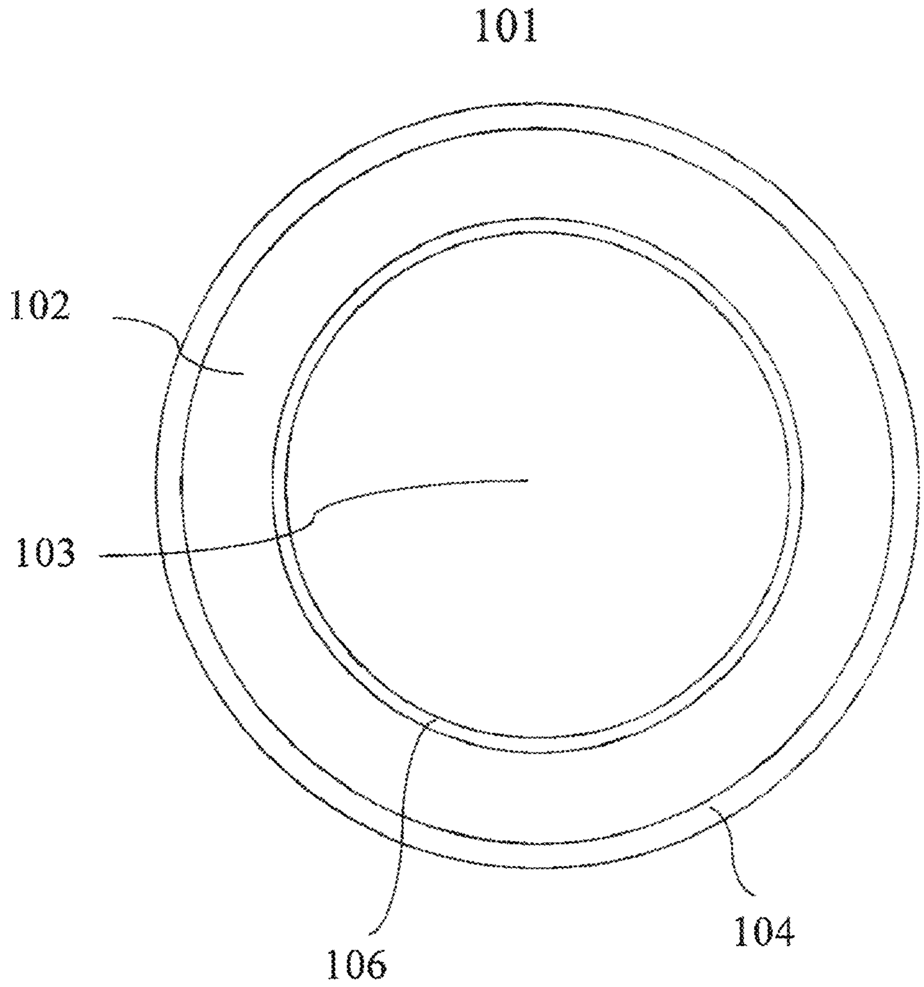
FIG. 1A and FIG. 1B comprise two views of the same ring 101.
Figure 1B:
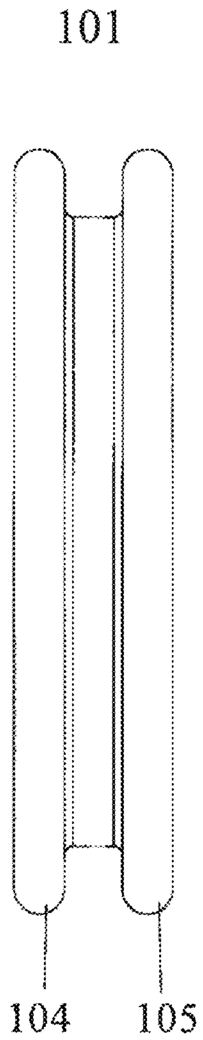
Figure 2:
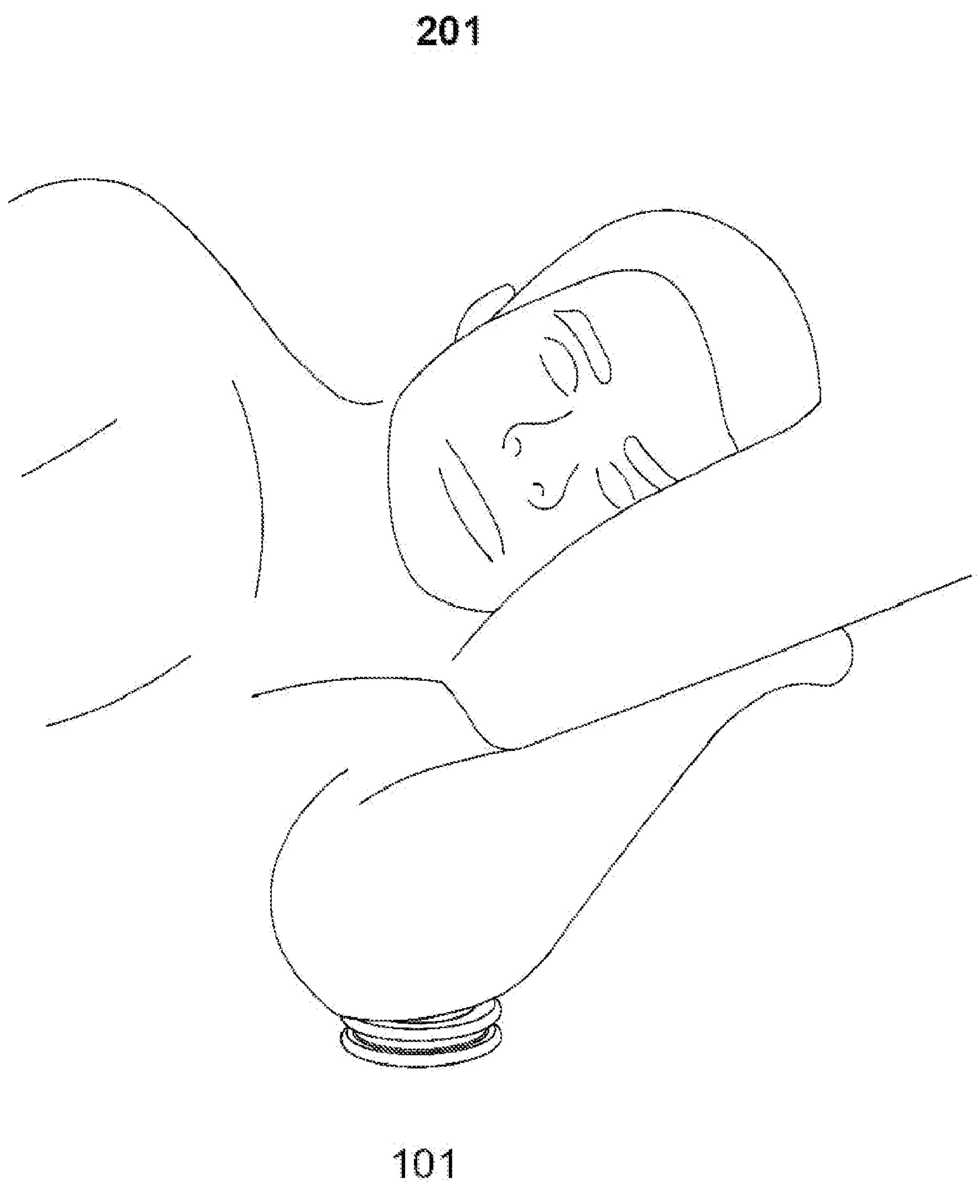
FIG. 2 shows the ring 101 in use in a sleeping individual. The sleeve 201 is not shown for clarity. The ring surrounds the lateral epicondyle 407 as also seen in FIG. 4. Side sleeping is the most common sleep position (60%). In this position, the weight of the arm (approximately 7-10 pounds) is applied to the lateral epicondyle, for much of the night. Ordinarily this position will not cause disability or pain. But if an initial injury has occurred, this position is aggravating. Furthermore, sleep positions are extremely habitual and are repeated every night. Wearing the ring allows patients to sleep in their usual positions without insomnia or restlessness. Most importantly, the ring protects the lateral epicondyle and its attachments from repetitive ongoing injury allowing rapid healing.
Figure 3:
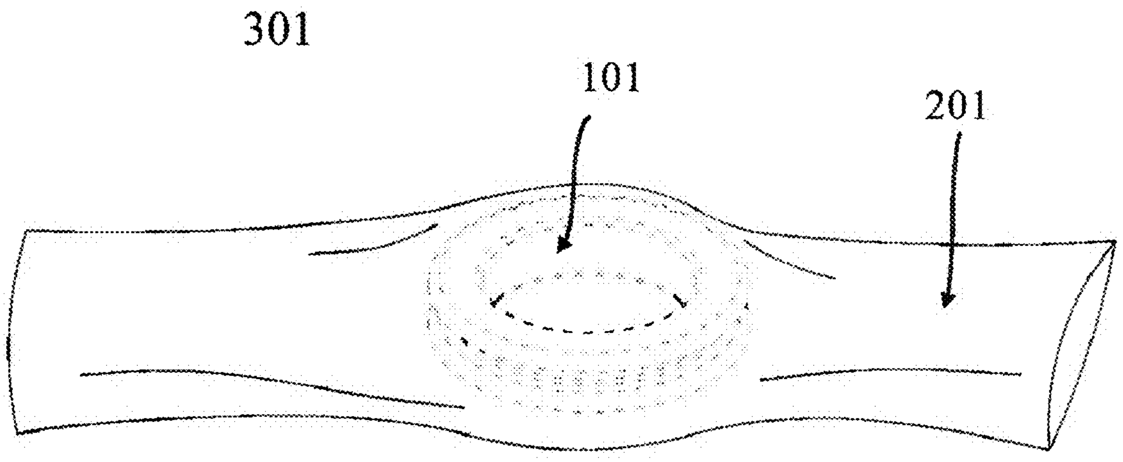
FIG. 3 shows the ring 101 centered in the tubular sleeve 201. The arm is inserted into the sleeve which is advanced towards the shoulder until centered over the lateral epicondyle. The lateral epicondyle is easily identified as the most prominent pointed structure on the outside of the elbow. It also can be identified by point tenderness. The sleeve extends above and below the elbow.
Figure 4:
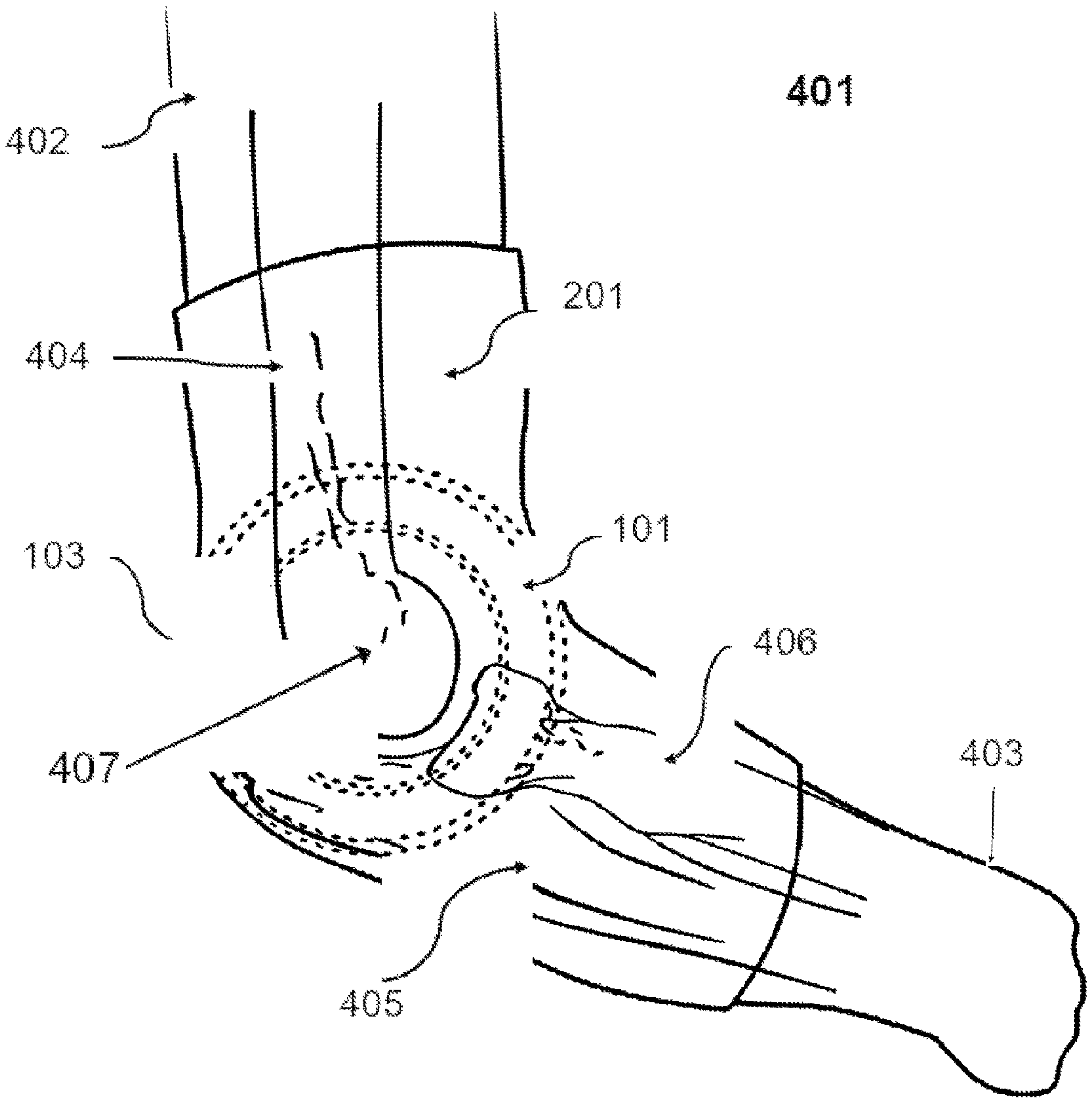
FIG. 4 shows the device in relation to the skeletal structure of the elbow 401. The elbow is comprised of three bones, the Humerus 404, the Radius 406, and the Ulna 405. The lateral epicondyle 407, is depicted on the outer aspect of the Humerus at the elbow.

The tennis elbow offloader ring, 101 is made of a soft pliable foam material for example, but not limited to closed-cell co-polymer (EVA) foam. The main active principal is the offset empty hole 103 that fits around and outside the lateral epicondyle 407 FIG. 4 for the purpose of limiting the application of any forces on the lateral epicondyle. In this embodiment a 2½ inch (68 mm) hole opening is used for the inner diameter of 103. The device can have another shape than a round hole to accomplish the unloading for example a "U" shape, with the goal that there will be no pressure on the lateral epicondyle. Other shapes can be included in consideration from oval to irregular and also custom 3D printed. The inner edges of 106, the ring's inner hole can be rolled over, or feathered with a quarter round router device. This slightly increases the hole diameter and will apply pressures gradually to the surrounding tissues. The outer edges 104, 105, can be flexible or rounded over to conform to the radius of the arm at the elbow. There should not be any material whatsoever or any physical substance between the lateral epicondyle bone, tendons, muscle or skin and the hole, that might apply pressure onto the lateral epicondyle region. The outer diameter of the ring is approximately 3⅝ inch (95 mm). The thickness overall is ⅝ inch (1.7 cm). A hard substance such as wood would be painful and should be avoided. The ring can be pliable to conform and adapt to the roundness of the arm around the outer elbow at the lateral epicondyle. The knit material for the sleeve is 3 inch wide most commonly. This knit sleeve is a stretchy elastomeric synthetic material used to maintain the ring in position as it conforms comfortably to complex anatomies and is self-adjusting. The ring itself is attached midway to the knit sleeve with hot melt adhesive, silicone glue or another binding method. This brace is easily applied by the patient prior to sleep and is comfortable to wear resulting in very high compliance, successful protection of the injured elbow tissues and rapid improvement of the root cause underlying tennis elbow.

The invention claimed is:

1. A therapeutic device to treat tennis elbow, comprising:

a) a brace configured to be worn around an elbow of a user and centered at a lateral epicondyle, comprising:

b) a circumferential tubular sleeve that is configured to extend above and below the elbow of the user;

c) a ring configured to offload the lateral epicondyle;

d) wherein the ring is designed to limit or eliminate compressive forces on the soft tissue attachments of the lateral epicondyle of the user during sleep;

e) wherein the ring has an empty central hole that is configured to encircle the lateral epicondyle;

f) wherein the ring is configured to be offset from the lateral epicondyle of the user to offload the lateral epicondyle and redistribute local pressures onto uninjured tissues surrounding the lateral epicondyle;

g) wherein the ring has a shape that is round, open-ended, oval, irregular or customizable;

h) wherein a material for the brace is non-allergenic and non-toxic to the local tissues;

i) wherein the material for the brace is also a breathable, elastic, stretchy, woven knit material configured to snugly hold and maintain a therapeutic position of the user's elbow;

j) wherein the ring is constructed from semi-rigid soft foam, gel or air bladder materials;

k) wherein the ring is fastened to the circumferential tubular sleeve;

l) wherein the circumferential tubular sleeve does not overlap the empty central hole of the ring such that the lateral epicondyle of the user is not covered by the brace when worn;

m) wherein inner edges of the ring are rounded such that the ring is configured to apply pressure gradually to the surrounding tissues when worn; and n) wherein outer edges of the ring are flexible or rounded over to conform to the elbow of the user.

2. A method to reduce nighttime pressures on a lateral epicondyle of a user, comprising:

a) applying a brace configured to shield injured and tender tissues on the lateral epicondyle of the user during sleep;

b) adapting the brace to any sleeping position;

c) limiting or eliminating contact between a bed and the lateral epicondyle of the user to facilitate healing, reduce pain, improve function, and promote recovery of tennis elbow;

d) wearing the brace while the user is unconscious and unable to consciously protect the lateral epicondyle from mechanical stress and aggravation occurring during sleep;

e) wherein the brace comprises a circumferential tubular sleeve that extends above and below an elbow of the user and a ring that offloads the lateral epicondyle;

f) wherein the ring has an empty central hole that encircles the lateral epicondyle of the user;

g) wherein the ring is fastened to the circumferential tubular sleeve;

h) wherein the circumferential tubular sleeve does not overlap the empty central hole of the ring such that the lateral epicondyle of the user is not covered by the brace when worn;

i) wherein the brace is configured to enhance sleep quality by mitigating the effects of pathological sleep positions.

* * * * *